(12) United States Patent
Tsang

(10) Patent No.: US 10,219,978 B2
(45) Date of Patent: Mar. 5, 2019

(54) ACUPUNCTURE DEVICES

(71) Applicant: Siu Kwong Tsang, Hong Kong (CN)

(72) Inventor: Siu Kwong Tsang, Hong Kong (CN)

( * ) Notice: Subject to any disclaimer, the term of this patent is extended or adjusted under 35 U.S.C. 154(b) by 210 days.

(21) Appl. No.: 15/394,828

(22) Filed: Dec. 30, 2016

(65) Prior Publication Data

US 2017/0189267 A1 Jul. 6, 2017

(30) Foreign Application Priority Data

Jan. 4, 2016 (CN) .................... 2016 2 0006437 U

(51) Int. Cl.
*A61N 1/04* (2006.01)
*A61H 39/00* (2006.01)
*A61N 1/36* (2006.01)
*A61H 39/08* (2006.01)
*A61N 1/05* (2006.01)

(52) U.S. Cl.
CPC ........... *A61H 39/002* (2013.01); *A61H 39/08* (2013.01); *A61N 1/0476* (2013.01); *A61N 1/0484* (2013.01); *A61N 1/36014* (2013.01); *A61H 2201/1604* (2013.01); *A61H 2201/5035* (2013.01); *A61H 2205/02* (2013.01); *A61N 1/0456* (2013.01); *A61N 1/0526* (2013.01)

(58) Field of Classification Search
CPC .. A61N 1/0476; A61N 1/0526; A61H 39/002; A61H 39/08–39/086
See application file for complete search history.

(56) References Cited

U.S. PATENT DOCUMENTS

2006/0167526 A1* 7/2006 Wan ..................... A61H 39/002
607/46

\* cited by examiner

*Primary Examiner* — George R Evanisko

(57) ABSTRACT

An acupuncture device can include a frame, an enclosure disposed on the frame to protect the frame, multiple stimulators mounted on the frame. The stimulators can be electrically coupled with a controller that transmits electric pulses to the stimulators for electro-acupuncture purpose. The size of the frame is adjustable to fit different body sizes of the users. The stimulators can be carried by the adjustment of the frame. The acupuncture device can also include one or more position references and the stimulators are positioned at relative distances from the position references. When the size of the frame is adjusted, the stimulators are carried by the frame to new positions that are at relative distances from the position references in proportionality with the extent of adjustment of the frame. Hence, the relative distance between a stimulator and a position reference in light of the size of the frame is maintained.

20 Claims, 4 Drawing Sheets

ACUPUNCTURE DEVICES

This application claims priority to Chinese utility model application no. CN201620006437.0 filed on Jan. 4, 2016. This application also incorporates by reference this Chinese utility model application no. CN201620006437.0 in its entirety.

TECHNICAL FIELD

Embodiments of this application relate to acupuncture devices or electro-acupuncture devices. Specifically, embodiments of this application relate to acupuncture devices that have multiple stimulators thereon. More specifically, the stimulators may be movable in proportion to an adjustment in size of the acupuncture device.

BACKGROUND

Acupuncture is a treasure of Chinese medicine. It has earned a world-renowned reputation based on its long history of well-established efficacy. Electro-acupuncture builds upon the foundation of traditional acupuncture's theories and techniques and combines acupuncture with modern theory of neural pulse electrotherapy. Electro-acupuncture is believed to enhance treatment results and the efficiency of acupuncture. The therapeutic theory of electro-acupuncture is that when the electric stimulators, such as needles, are placed at acupuncture points (sometimes also referred as nerve stimulation points), the electric pulses can induce rapid and widespread reactions to the cells and the nerve system. Electro-acupuncture is believed to be able to strengthen nerve signal transmission, promote blood and lymph intercellular transportation, nurture nerve tissue, relieve vascular spasm, dilate blood vessels, improve microcirculation, mitigate nerve fiber edema, promote local tissue metabolism, and promote restoration of neuromuscular function.

Traditional acupuncture technique, such as scalp acupuncture, can include placing stimulators such as needles at different acupuncture points to treat and/or prevent different mental and body disorders. It typically involves an acupuncture professional's or a Chinese medical practitioner's selection of stimulation points based on traditional acupuncture points in accordance with Chinese medicine theories. While the treatment result is established and proven, this type of acupuncture or electro-acupuncture has a certain limitations. For example, the stimulators usually need to be relatively accurately placed at acupuncture points in order to achieve better results. However, the general public is often unfamiliar with the precise locations of acupuncture points or even does not have ideas where the acupuncture points are. Hence, acupuncture or electro-acupuncture conventionally has to be operated by medical or acupuncture professionals.

SUMMARY

Acupuncture devices described hereinbelow address the aforementioned drawbacks. In one aspect, an acupuncture device can include a frame that is retractable and extendable, an enclosure placed on the frame to protect the frame, a first type of stimulators mounted on the frame, and a second type of stimulators also mounted on the frame. The first type of stimulators can be a type of position reference component that is marked differently than the second type of stimulators so that regular non-professional users can recognize the first type of stimulators. The second types of stimulators can be movable by the extension or the retraction of the frame.

In another aspect, the acupuncture device can be of a helmet shape. The frame can have an adjustable size. There can be a first position reference and a second position reference mounted on the frame. The two position references are spaced apart from each other by a reference distance. And the reference distance can be adjusted in accordance with proportion of the adjustment of the size of the frame. The two position references are intended to allow regular users to place them at places that are easily identifiable, such as at the vertex of their head, at the middle of the forehead, or slightly above the ears, etc.

The acupuncture device can include multiple acupuncture stimulators mounted on the frame. Each of the stimulators is positioned apart from the first position reference by a respective distance. The acupuncture device can be configured in a manner such that when the size of the frame is adjusted, the reference distance is adjusted by a ratio. And the respective distance between a stimulator and a position reference is also adjusted substantially by the same ratio. The stimulators can be mounted on the frame at predetermined locations corresponding to certain acupuncture points in accordance of traditional Chinese acupuncture theories. Hence, when the position references are aligned at certain easily identifiable locations and the frame is adjusted according to the size of the user's body, all of the stimulators are carried by the adjustment of the frame proportionally so that the stimulators will be placed at relatively accurate locations of acupuncture points without the user's knowledge of the precise location of acupuncture points or even any knowledge of acupuncture points at all.

The acupuncture devices described herein have several advantages. First, the appropriate electric stimulation sites such as acupuncture points can be predetermined during manufacture by professionals for the treatment or prevention of various diseases and disorders. Second, the acupuncture devices are safe, reliable and simple to use. The devices do not require expertise in acupuncture to use. The devices can also fit different body sizes of different people of different genders and ages.

The acupuncture devices allow users to perform simple adjustment based on the size of the users' body part, then the stimulators can be positioned at the intended acupuncture points.

Also, the acupuncture devices can include an enclosure that is made of a material that is flexible, elastic and resilient. As such, the enclosure is able to enclose the frame and exert slight pressure to the frame and to the stimulators such that the stimulators can be secured in place and can have close contact with the user's skin. This prevents the stimulators from being loosened from the skin so that this can ensure the electric pulses can be transmitted continuously.

For needle type stimulators, the tip of the needles can be smooth and circular so that the needles will not cause pain or penetrate the skin. This allows painless, effective, simple, and practical use of the acupuncture devices.

DETAILED DESCRIPTION

Figure 1:
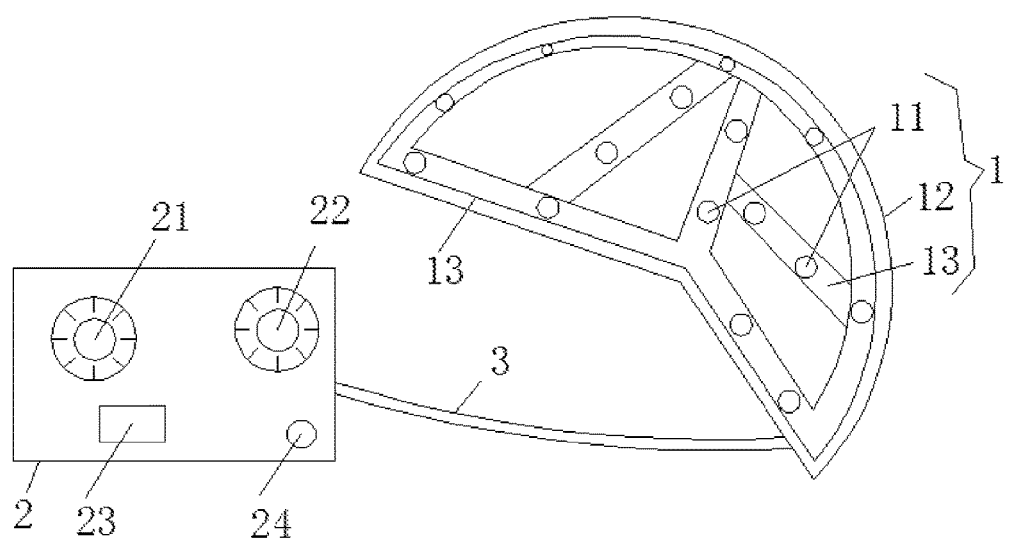
FIG. 1 is a simplified illustration on an acupuncture device coupled with a controller in accordance with an embodiment.
Figure 2:
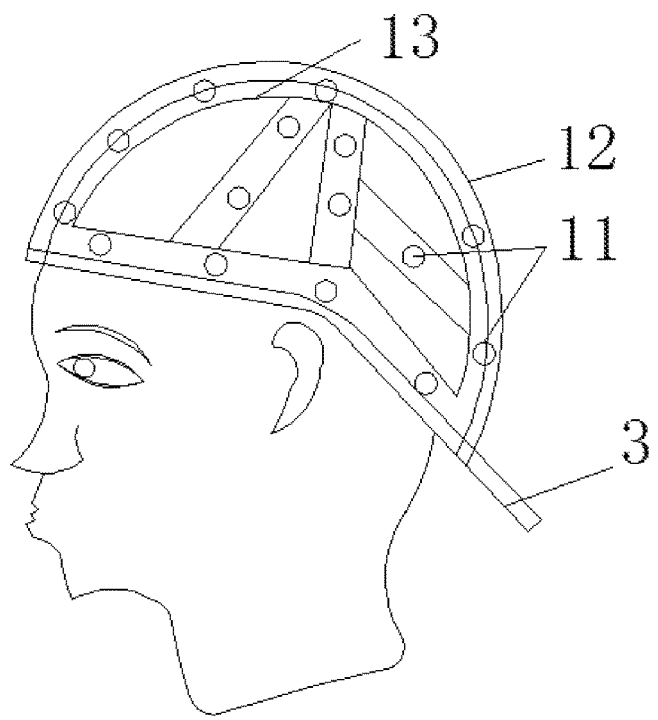
FIG. 2 is a simplified side view of a user wearing an acupuncture device in accordance with an embodiment.
Figure 3:
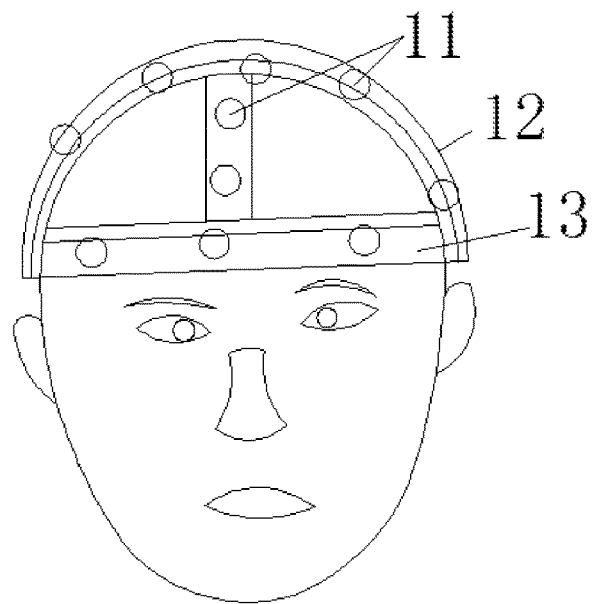
FIG. 3 is a simplified front view of the user wearing the acupuncture device.
Figure 4:
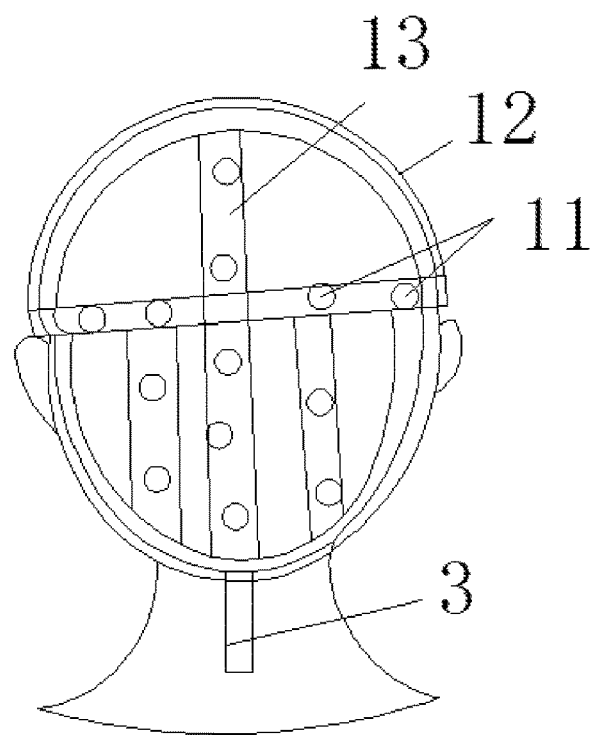
FIG. 4 is a simplified back view of the user wearing the acupuncture device.

The following description is made for the purpose of illustrating the general principles of the invention and should not be taken in a limiting sense. The scope of the invention is best determined by reference to the appended claims.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

With reference to FIGS. 1-7, an acupuncture device can be a helmet-shaped acupuncture device 1 that can be coupled with a controller 2. And electrical wires 3 may removably connect the helmet-shaped acupuncture device 1 and the controller 2. The helmet-shaped acupuncture device 1 can include multiple stimulators 11 that can be of needle shape, an enclosure 12, and frame 13. The enclosure 12 can be disposed on the frame 13, which is extendable and retractable. The stimulators 11 can be mounted on the frame 13. The controller 2 can be electrically coupled with the stimulators 11 via the electrical wires 3. The controller can provide energy and regulate electric pulses sent to the stimulators 11. Suitable electric pulses are applied to the stimulators 11 for electro-acupuncture purposes.

Figure 6:
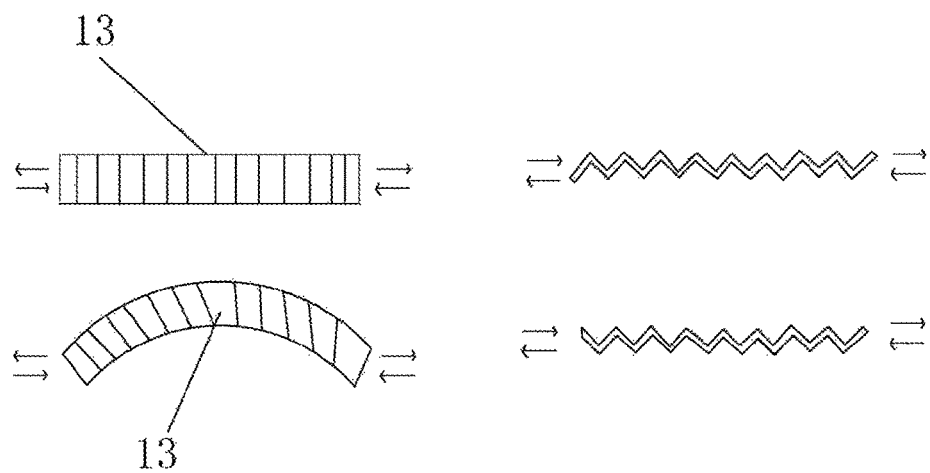
FIG. 6 illustrates the extension and retraction of a frame of an acupuncture device in accordance with an embodiment.

Specifically, the frame 13 can be extended and retracted. Frame 13 can be made of rubber, plastic, or polymer materials or metallic thin strips. The frame 13 may have one or more frame pieces. Each frame strip can be of a zigzag type or a corrugation type so that it has flexibility and scalability. Frame strips can be straight or can be curved, as best shown in FIG. 6.

The enclosure 12 can serve as an elastic cover of the helmet-shaped electrical acupuncture device 1. It may be made of any elastic and flexible materials including, but not limited to, rubber or plastic. The enclosure 12 encloses the frame 13 and stimulators 11. When the helmet-shaped electrical acupuncture device 1 is worn by a user, the elasticity and flexibility of the enclosure 12 can create sufficient pressure so that the stimulators 11 can closely and precisely contact the selected points of stimulation of the scalp of the user. The enclosure 12 also provides comfort, durability and aesthetics to the helmet-shaped electrical acupuncture device 1. However, it is understood that enclosure 12 can also be made of hard material such as metal.

The stimulators 11 can comprise a needle body and needle holder. The metallic or conductive needle body, through the needle holder, is mounted on the inner surface of the frame 13. Stimulators 11 mounting on the frame can allow the stimulators to be moved proportionally instead of in some arbitrary or irregular manners. The tip of needle body can be generally circular. There can be a variety of needle types. For example, a straight needle stimulator can have a needle holder with a diameter of about 0.8-2.0 centimeters and a needle body with a diameter of about 0.15-0.3 millimeters. A tapered needle stimulator can have a needle holder with a diameter of about 0.8-2.0 centimeters and a needle body that is tapered from the needle holder. The tip of the needle body can be blunt or circular. A mixed type needle can have a needle holder with a diameter of about 1-3 centimeters and a needle body that combines the needle body of a straight needle and a tapered needle. While stimulators 11 are described as having a needle shape, it is understood that the stimulators 11 are not necessarily of needle shape. For example, the stimulators 11 can be adhesive electrical stimulative stickers that can be circular or rectangular in shape. The circular type stickers can have a diameter of about 1.5-3 centimeters while the rectangular type stickers can be about 2-3 centimeters by 3-5 centimeters. While the above stimulators are described in accordance with some embodiments of the present invention, it is understood that the embodiments of the present invention can also include various other different stimulators and/or needles. Also, each embodiment of the present invention may have one or more types of stimulators in different combinations, configurations and arrangements.

The stimulators 11 can be arranged in pairs with two stimulators as a pair. Each pair is connected using wires and acts as the positive and negative poles. The pairs are connected to the controller 2 via wires 3 so that the controller can transfer suitable electric pulses to the stimulators 11 and stimulate the contact regions of the user.

Figure 7A:
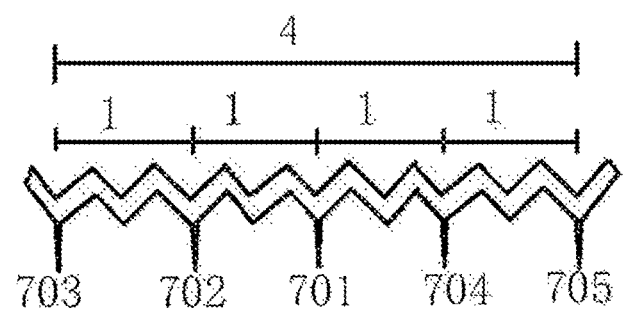
FIGS. 7A and 7B illustrate how stimulators can be carried proportionally by an extension or retraction of a frame.
Figure 7B:
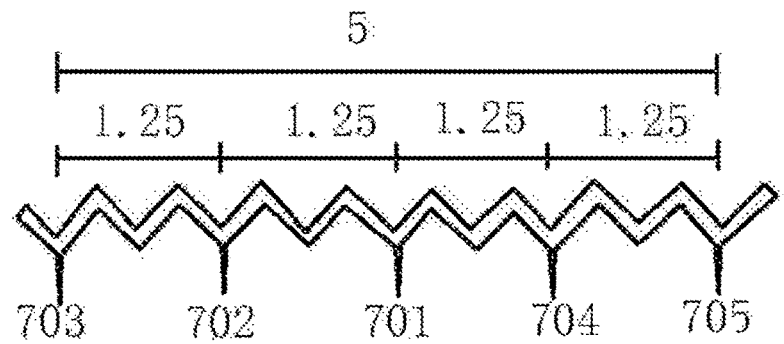

Referring to FIGS. 7A and 7B, a plurality of stimulators 11, such as needles 701, 702, 703, 704, and 705, can be mounted on each frame strip 13. The plurality of needles 701-705 can comprise a position reference needle 701 and other regular needles 702-705. The position reference needle 701 can have a special mark such as having a different color for user to distinguish it. While the position reference structure is described as position reference needle or stimulator, it does not have to be a stimulator that carries out acupuncture function. It can merely be a structure for position alignment. Other needles 702-705 can move in relative to the position reference needle 701 when the adjustable frame strip 13 is elongated or shortened. As such, the distance between a regular needle and the position reference needle 701 can be proportionally adjusted.

Figure 5:
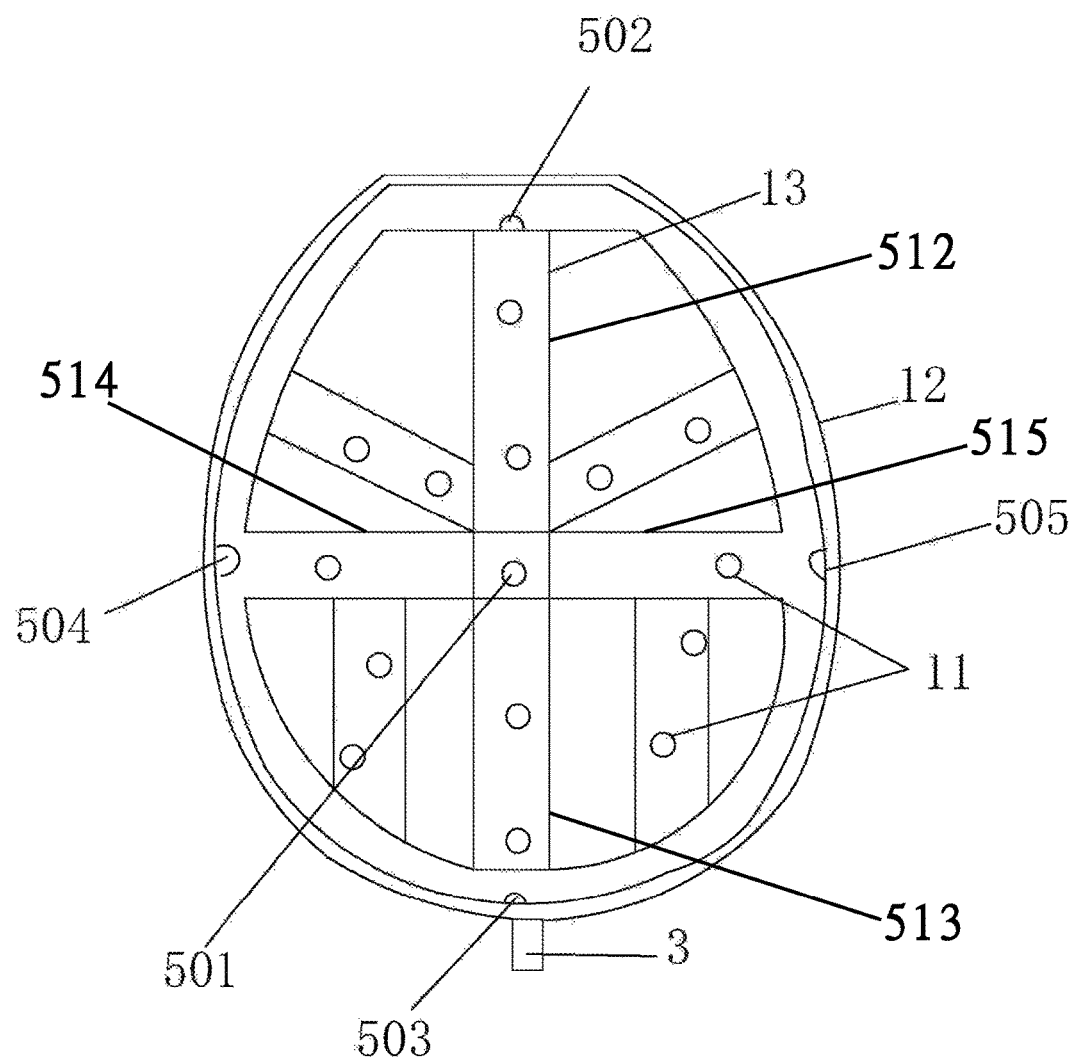
FIG. 5 is a simplified top view of an acupuncture device in accordance with an embodiment.

FIG. 5 illustrates the locations of several position reference stimulators on an acupuncture device in accordance with a described embodiment. The helmet-shaped electrical acupuncture device 1 can comprise a number of position reference stimulators, such as five position reference stimulators 501, 502, 503, 504 and 505. The first position reference stimulator 501 is located at the central of the acupuncture device 1, and the four other position reference stimulators 502, 503, 504 and 505 are respectively located at the front, back, left and right of the acupuncture device 1. All other regular stimulators 11 are located at a distance in relative to one or more position reference stimulators. The locations of those regular stimulators 11 in relative to the position reference stimulators 501-505 can be adjusted proportionally in accordance with the elongation or shortening of the frame 13.

Referring to FIG. 1, the controller 12 can be provided with a user interface, an electric pulse generator and a power supply unit. The stimulators 11 are connected to the electric pulse generator via wires 3. The user interface of the controller 12 can comprise a pulse strength adjustment control 21, a waveform adjustment control 22, a power switch 23, and a power indicator 24.

The waveform adjustment control 22 can be used to choose different types of electric pulses sent to the stimulators 11, including, but not limited to, continuous waves, intermittent waves, and alternating waves. The controller 12 may further comprise a numbers of predetermined routines such various treatment modes and prevention modes. In those modes, the controller 12 can automatically arrange and cycle different waveforms and transmit those electric pulses to the stimulators. For example, in a predetermined prevention mode, the continuous waves, intermittent waves, and alternating waves will be sent to the stimulators at intervals of 10 minutes for each waveform. The three waveforms will be circulating in such routine. In another example, a treatment mode requires the user to manually choose one of the waveforms. Then the user may choose an intensity level of 0 to 9 for the electric pulses by changing the pulse strength adjustment control 21. In an embodiment, the controller 2 can further comprise an automatic timing knob for users to select duration of operation from 0 to 60 minutes.

In one embodiment, continuous waves may refer to electric pulses having a frequency of 2-500 Hz. Intermittent waves may refer to electric pulses having a frequency of 2-500 Hz with the presence of electric pulses for 10-30 seconds and a pause of 3-10 seconds. Alternating waves may refer to electric pulses having a low frequency of 2-20 Hz and a high frequency of 20-500 Hz. And the low frequency and the high frequency are alternating by a period of 5-10 seconds. While three particular examples of waveforms are described, it is understood that those three waveforms are for reference only and embodiments of the present invention can include various other waveforms.

The power source of the embodiments can generally be 6V-9V direct current or household alternating current with a transformer stepped down to a voltage that is safe to users.

FIGS. 7A and 7B illustrates how different users only need to make a simple adjustment in order to accurately place all electric stimulators 11 on the appropriate locations of the acupuncture points, which can sometimes also be referred as nerve stimulation points, on a region of the user, such as on the head of the user. An example frame 13 can include multiple stimulators 11. Among the stimulators 11, one or more of them can be position reference stimulators such as a position reference stimulator 701, which has a special mark or symbol on it such as having a different color so that users can recognize this is a position reference stimulator 701. This position reference stimulator 701 is for the user to use as a reference for position. And other regular stimulators 702-705 provided on the frame 13 are located on specific locations such that the relative distance between a regular stimulator 702, 703, 704, or 705 and the position reference stimulator 701 is proportional to the relative distance between two acupuncture points on human body. The stimulators are located at predetermined locations that correspond to certain acupuncture points, such as those that are believed to be particularly effective for acupuncture purposes according to traditional Chinese medicine theories. As such, the stimulators can be located unevenly on an acupuncture device, as shown in various illustrative figures in this application. For example, in FIG. 5, various stimulators 11 are located at asymmetrical locations throughout the device because the stimulators 11 may be located at predetermined locations according to traditional Chinese medicine theories.

From a reference position as defined by the position reference stimulator 701, the frame 13 can be extended or retracted through the frame's zigzag structure or its corrugation structure. When the frame 13 extends or retracts, it will carry the regular stimulators 702, 703, 704 and 705 accordingly so that those regular stimulators are moved proportionally in accordance with the extent of the extension or retraction of the frame 13.

For example, FIG. 7A can be a frame strip, which can be a partial frame of the entire frame. The partial frame can have a first stimulator 701 positioned at the center of the partial frame. In this example, the first stimulator 701 is the position reference stimulator and can be stationary. And the rest of the second to fifth stimulators 702-705 are movable in relative to the first stimulator 701. Each stimulator is separated from each other by one inch. When a user pulls the partial frame, it can be extended by a length, such as by one additional inch, as shown in FIG. 7B. In this situation, the second to the fifth movable stimulators 702, 703, 704 and 705 will be carried proportionally by the degree of extension of the partial frame. Hence, a movable stimulator will be carried to a second location in relative to first stimulator 701. As a result, each stimulator now is separated from each other by 1.25 inches.

Generally, position reference stimulators on the frame are usually located at reference positions that are easily identifiable by regular users, such as at the center point or the vertex of the top of a head. And the regular stimulators are positioned in relative distances from one or more position reference stimulators so that the regular stimulators are located at various acupuncture points that can be predetermined by professionals during the manufacture of the acupuncture devices. Hence, for the acupuncture devices described herein, regular users only need to align the position reference stimulator(s) at some easily identifiable location(s), then extend or retract the frame to adjust the size of the acupuncture device to fit the size of their body, such as their head. The rest of the stimulators will be proportionally carried by the adjustment of the frame and automatically be moved accurately to the acupuncture points of the users in accordance to the degree of adjustment of the size of the frame. Hence, regular users who are not familiar with various acupuncture points can use this acupuncture device to carry out acupuncture or electro-acupuncture without a professional to accurately place the stimulators at various acupuncture points for the users.

The following examples are described in conjunction with actual names of acupuncture points.

On the head of a human body, Baihui point (point GV20 according to Standard Acupuncture Nomenclature, Second Edition, published by World Health Organization in 1993) is located at the midpoint of two ears, i.e. the vertex of head. Shenting point (GV 24) is located at the midpoint of the front of the forehead near the midpoint of two eyebrows. Fengfu point (GV16) is located on the posterior midline of the head at a recessed location between neck muscles at the back of the head. Niezuo point is located on the left side of the head right above the tip of the left ear. Nieyou point is located on the right side of the head right above the tip of the right.

A user can wear an example acupuncture device 1 on his/her head and position a first position reference stimulator at the easily identifiable Baihui point, which is located at the vertex of the head. Then the user can extend or retract a frame strip so that another position reference stimulator can be positioned at the Shenting point at the forehead. After two position reference stimulators are placed properly, the user can then extend or retract the frame to adjust the size of the acupuncture device 1 according to the size of his/her head. As the frame is adjusted according to the size of the user's head and the two position reference stimulators are positioned properly, all other regular stimulators will be automatically placed at other different less easily identifiable acupuncture points on the user's head. Coupled with the flexibility and elasticity of the enclosure 12 that applies slightly compressive force to the stimulators, the stimulators can be in close contact with the skin and be secured in position. In addition, the tip of the stimulators can be blunt or in a smooth circular shape so that those needle-shaped stimulators do not penetrate the skin or cause pain to the users. All these features provide a safe, comfortable, and easy-to-use acupuncture device to achieve the best prevention and treatment results.

In another example, which can be illustrated by FIG. 5, the acupuncture device 1 can have five position reference stimulators 501, 502, 503, 504, and 505. A user can wear the acupuncture device 1, place the first position reference stimulator 501 at Baihui point, which is located at the vertex of the head. Then the user can extend or retract the frame strip 512 to place the second position reference stimulator 502 Shenting point at the forehead. Then the user can extend or retract the frame strip 513 to place the third position reference stimulator 503 at the Fengfu point, which is located at the back of the head. Further, the user can extend or retract the frame strips 514 and 515 to place the fourth and fifth position reference stimulators 504 and 505 respectively at Niezuo point and Nieyou point, which are located near the ears. Based on the proportionality of the retraction or extension of the frame strips, all of the rest of the stimulators 11 will be automatically be carried to their respective acupuncture points.

The foregoing description of the embodiments of the present invention has been presented for the purpose of illustration and description. It is not intended to be exhaustive or to limit the invention to the precise form disclosed. Many modifications and variations are possible in light of the above teachings. The numerical values described in the description are only for illustration purpose and should not be understood as limiting the invention to the precise numbers. It is intended that the scope of the present invention not be limited by this detailed description, but by the claims and the equivalents to the claims appended hereto.

It should also be understood that various omissions, substitutions, and changes in the form of the detail of the apparatus, system, and/or method as illustrated as well as the uses thereof, may be made by those skilled in the art, without departing from the spirit of the present invention. Consequently, the scope of the present invention should not be limited to the disclosed embodiments, but should be defined by the appended claims.

The invention claimed is:

1. An acupuncture device, comprising:
a frame that is retractable and extendable;
an enclosure disposed on the frame;
a first type of stimulators mounted on the frame, the first type of stimulators comprising a first position-reference stimulator and a second position-reference stimulator positioned apart from the first position-reference stimulator by a reference distance, the reference distance is adjustable by an adjustment of a size of the frame; and
a second type of stimulators mounted on the frame, wherein the second type of stimulators is marked differently than the first type of stimulators and wherein the second type of stimulators are adapted to be movable by an extension or a retraction of the frame, the second type of stimulators comprising a first acupuncture stimulator and a second acupuncture stimulator, the first acupuncture stimulator positioned apart from the first position-reference stimulator by a first distance, the second acupuncture stimulator positioned apart from the second position-reference stimulator by a second distance,
wherein the size of the frame is adjustable such that when the reference distance is adjusted by a ratio, the frame is configured to automatically adjust the first and second distances by substantially the same ratio.

2. The acupuncture device as recited in claim 1, wherein the first type of stimulators is colored differently than the second type of stimulators.

3. The acupuncture device as recited in claim 1, wherein the second type of stimulators is needle-shaped.

4. The acupuncture device as recited in claim 1, wherein the second type of stimulators is adapted to be electrically coupled to a controller so that the second types of stimulators is adapted to receive electric pulses from the controller.

5. The acupuncture device as recited in claim 1, wherein the controller is adapted to send multiple types of electric pulses.

6. The acupuncture device as recited in claim 1, wherein the frame is a zigzag type.

7. The acupuncture device as recited in claim 1, wherein the frame is a corrugation type.

8. A helmet comprising:
a frame having an adjustable size;
a first position reference and a second position reference mounted on the frame, the first position reference being positioned apart from the second position reference by a reference distance, the reference distance capable of being adjusted by an adjustment of the size of the frame;
a first acupuncture stimulator mounted on the frame, the first acupuncture stimulator being positioned apart from the first position reference by a first distance; and
a second acupuncture stimulator mounted on the frame, the second acupuncture stimulator positioned apart from the second position reference by a second distance;
wherein the helmet is configured such that:
when the size of the frame is adjusted such that the reference distance is extended by a ratio, the frame is configured to automatically adjust and extend the first and second distances by substantially the same ratio.

9. The helmet as recited in claim 8, further comprising an enclosure disposed on the frame.

10. The helmet as recited in claim 9, wherein the enclosure is composed of rubber.

11. The helmet as recited in claim 8, wherein the first and second position references are acupuncture stimulators that are marked differently than the first acupuncture stimulator and than the second acupuncture stimulator.

12. The helmet as recited in claim 8, wherein the first position reference is adapted to align a vertex of a head.

13. The helmet as recited in claim 8, wherein the helmet comprises five position references, the five position references include the first position reference, the second position reference, and three additional position references, the five position references are located respectively at a center, a front, a back, a left side and a right side of the helmet.

14. The helmet as recited in claim 8, wherein first acupuncture stimulator and the second acupuncture stimulator are adapted to be electrically coupled to a controller so that the first acupuncture stimulator and the second acupuncture stimulator are adapted to transmit electric pulses received from the controller.

15. A method for using an acupuncture device, the acupuncture device comprising (i) a frame having an adjustable size, (ii) a first position reference and a second position reference mounted on the frame, the first position reference being positioned apart from the second position reference by a reference distance, the reference distance capable of being adjusted by an adjustment of the size of the frame, (iii) a first acupuncture stimulator mounted on the frame, the first acupuncture stimulator being positioned apart from the first position reference by a first distance; and (iv) a second acupuncture stimulator mounted on the frame, the second acupuncture stimulator positioned apart from the second position reference by a second distance, wherein the size of the frame is adjustable such that when the reference distance is extended by a ratio, the frame is configured to automatically adjust and extend the first and second distances by substantially the same ratio, the method for using the acupuncture device comprising:
positioning the first position reference at a first location; and
adjusting the size of the frame to position the second position reference at a second location such that the reference distance is adjusted by the ratio and the first and second distances are also adjusted by substantially the same ratio.

16. The method as recited in claim 15, further comprising connecting the acupuncture stimulators to an electrical controller that is adapted to transmit electric pulses to the acupuncture stimulators.

17. The method as recited in claim 16, further comprising selecting a type of electric pulses from multiple types of electric pulses.

18. The method as recited in claim 15, wherein the first location is a vertex of a head.

19. The method as recited in claim 15, wherein the first location is a Baihui acupuncture point.

20. The method as recited in claim 15 further comprising positioning a third position reference of the acupuncture device to a third location.

* * * * *